United States Patent [19]

Ishida et al.

[11] Patent Number: 5,686,452

[45] Date of Patent: Nov. 11, 1997

[54] INDANE DERIVATIVE AND PROCESSES FOR PREPARING THE SAME

[75] Inventors: Akihiko Ishida, Urawa; Koichi Homma, Tokyo-to; Michihisa Yato, Urawa; Shinsuke Nishiyama; Fumikazu Okumura, both of Ohmiya, all of Japan

[73] Assignee: Tanabe Seiyaku Co., Ltd., Osaka, Japan

[21] Appl. No.: 767,392

[22] Filed: Dec. 16, 1996

Related U.S. Application Data

[63] Continuation of Ser. No. 365,428, Dec. 28, 1994, abandoned.

[30] Foreign Application Priority Data

Dec. 28, 1994 [JP] Japan ................. 5-335250

[51] Int. Cl.$^6$ ................. A61K 31/50; C07D 237/14
[52] U.S. Cl. ................. 514/247; 544/239
[58] Field of Search ................. 544/239; 514/247

[56] References Cited

U.S. PATENT DOCUMENTS

| | | | |
|---|---|---|---|
| 4,816,454 | 3/1989 | Zoller et al. | 514/211 |
| 4,820,705 | 4/1989 | Nickl et al. | 514/247 |
| 5,030,652 | 7/1991 | Iwakuma et al. | 514/510 |
| 5,179,018 | 1/1993 | Bogard, Jr. et al. | 530/388.15 |
| 5,409,956 | 4/1995 | Yoshida et al. | 514/562 |
| 5,605,901 | 2/1997 | Ishida et al. | 514/247 |

FOREIGN PATENT DOCUMENTS

| | | |
|---|---|---|
| 8654612 | 10/1986 | Australia . |
| 0194548A3 | 9/1986 | European Pat. Off. . |
| 0579059A1 | 1/1994 | European Pat. Off. . |
| 0589037A1 | 3/1994 | European Pat. Off. . |
| 63-23853 | 1/1988 | Japan . |
| WO9215558 | 9/1992 | WIPO . |

OTHER PUBLICATIONS

CA 123: 143910 Indane derivatives . . . their preparation. Ishida et al., Dec. 27, 1994.
Dorland's Medical Dictionary, 27th Ed, pp. 557, 596, 1081, 1985.

*Primary Examiner*—Joseph McKane
*Attorney, Agent, or Firm*—Birch, Stewart, Kolasch & Birch, LLP

[57] ABSTRACT

Disclosed are an indane compound represented by the formula:

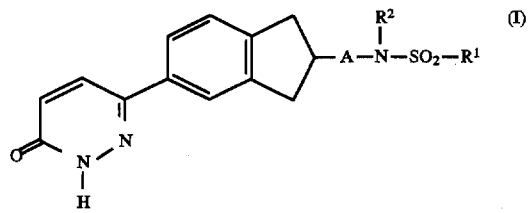

wherein $R^1$ represents a lower alkyl group, a lower alkenyl group or a substituted or unsubstituted monocyclic aromatic heterocyclic group having nitrogen atom as a hetero atom; $R^2$ represents hydrogen atom or a lower alkyl group; and A represents a lower alkylene group, or a pharmaceutically acceptable salt thereof and processes for preparing the same.

21 Claims, No Drawings

INDANE DERIVATIVE AND PROCESSES FOR PREPARING THE SAME

The present application is a continuation of U.S. application Ser. No. 08/365,428 filed on Dec. 28, 1994, now abandoned.

BACKGROUND OF THE INVENTION

This invention relates to a novel indane derivative having an action of protecting from endotoxin shock and/or an action of curing nephritis and processes for preparing the same.

In Japanese Provisional Patent Publication No. 23853/1988, it has been disclosed that benzenesulfonamidindane compounds such as 6-(2-benzenesulfonamid-indan-5-yl)-4,5-dihydro-pyridazin-3(2H)-one exhibit antithrombotic actions. In PCT Provisional Patent Publication No. 15558/1992, it has been disclosed that benzenesulfonaminoalkylindane compounds such as 6-[2-[(4-chlorophenyl)sulfonylaminomethyl]-indan-5-yl]-3-oxo-2,3,4,5-tetrahydropyridazine have antagonistic actions on thromboxane $A_2$.

On the other hand, as an agent for curing endotoxin shock which occurs in a patient seriously infected with gram-negative bacteria, there have been conventionally used steroid hormones, aprotinin (a protease inhibitor) and dobutamine (a cardiac).

Further, as an agent for curing nephritis, there have been conventionally used prednisolon (asteroid agent), cyclophosphamide (an immunosuppressant), dipyridamole, dilazep (antiplatelets) and haperin (an anticoagulant).

SUMMARY OF THE INVENTION

An object of the present invention is to provide a novel indane derivative having an excellent action of protecting from endotoxin shock and/or an excellent action of curing nephritis, processes for preparing the same and a synthetic intermediate of the same.

That is, the present invention is concerned with an indane derivative represented by the formula (I):

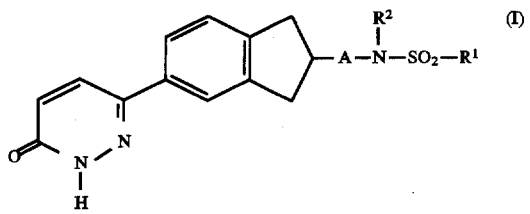

wherein $R^1$ represents a lower alkyl group, a lower alkenyl group or a substituted or unsubstituted monocyclic aromatic heterocyclic group having nitrogen atom as a hetero atom; $R^2$ represents hydrogen atom or a lower alkyl group; and A represents a lower alkylene group, a pharmaceutically acceptable salt thereof, and processes for preparing the same.

DESCRIPTION OF THE PREFERRED EMBODIMENTS

In the following, the present invention is explained in detail.

In the desired compound (I) of the present invention, as the substituted or unsubstituted monocyclic aromatic heterocyclic group having nitrogen atom as a hetero atom, there may be mentioned, for example, a pyridyl group which may be substituted by 1 to 4 groups selected from the group consisting of a lower alkyl group, a halogeno-lower alkyl group, a lower alkoxy group, a lower alkylthio group, hydroxy group, mercapto group, cyano group, amino group, substituted amino group (for example, a lower alkylamino group, a di-lower alkylamino group, a lower alkylcarbonylamino group), a halogen atom, carboxy group, a lower alkoxycarbonyl group, a lower alkylcarbonyloxy group, a lower alkylcarbonyl group, carbamoyl group, a di-lower alkylcarbamoyl group, and phenoxy group.

In the desired compound (I) of the present invention, as a preferred compound, there may be mentioned a compound represented by the formula (I) in which $R^1$ is an alkyl group having 1 to 4 carbon atoms, a vinyl group or a pyridyl group; $R^2$ is hydrogen atom or an alkyl group having 1 to 6 carbon atoms; and A is an alkylene group having 1 to 4 carbon atoms.

As a more preferred compound, there may be mentioned a compound represented by the formula (I) in which $R^1$ is a vinyl group, $R^2$ is hydrogen atom or an alkyl group having 1 to 3 carbon atoms and A is an alkylene group having 1 to 4 carbon atoms.

In the desired compound (I) of the present invention, two kinds of optical isomers based on an asymmetric carbon atom exist. Both of these optical isomers and a mixture thereof are included in the present invention.

The desired compound (I) of the present invention can be used for medical purposes either in a free form or in the form of a pharmaceutically acceptable salt thereof. As the pharmaceutically acceptable salt, there may be mentioned inorganic acid salts such as hydrochloride, phosphate and hydrobromide, and organic acid salts such as acetate, succinate, fumarate and methanesulfonate.

The desired compound (I) of the present invention can be administered either orally or parenterally, and it can be used as a medical preparation by mixing it with an excipient suitable for oral or parenteral administration. The medical preparation may be a solid preparation such as a tablet, a capsule and a powder, or a liquid preparation such as a solution, a suspension and an emulsion. Further, when the desired compound (I) is administered parenterally, it can be used in the form of an injection.

The dose varies depending on age, body weight and state of a patient and disease conditions of a patient, but, in general, the dose per day is preferably 1 to 300 mg/kg, particularly 3 to 100 mg/kg in the case of oral administration, and it is preferably 0.01 to 50 mg/kg, particularly 0.1 to 20 mg/kg in the case of parenteral administration.

According to the present invention, the desired compound (i) can be obtained by Method (A), i.e., reacting an amine compound represented by the formula (II):

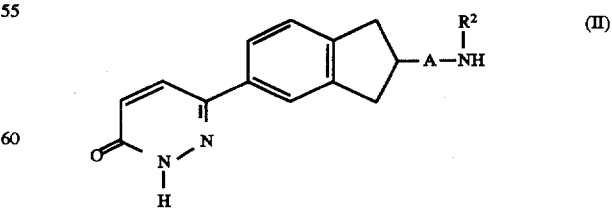

wherein $R^2$ and A have the same meanings as defined above, or a salt thereof, with a sulfonic acid derivative represented by the formula (III):

$R^1-SO_2X$  (III)

wherein $R^1$ has the same meaning as defined above; and X represents a reactive residue, or by Method (B), i.e., oxidizing a compound represented by the formula (IV):

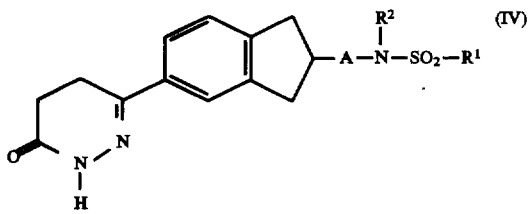

wherein $R^1$, $R^2$ and A have the same meanings as defined above.

As the reactive residue (X) of the sulfonic acid derivative (III), there may be mentioned a group which splits off nucleophilically, for example, a halogen atom, an alkoxy group, a lower alkylsulfonyloxy group, benzenesulfonyloxy group, a lower alkyl group-substituted benzenesulfonyloxy group and trifluoromethanesulfonyloxy group.

As the salt of the amine compound (II), there may be used, for example, a salt with an inorganic acid such as hydrochloric acid, hydrobromic acid and sulfuric acid, and a salt with an organic acid such as succinic acid and fumaric acid.

Method (A)

The reaction of the amine compound (II) or a salt thereof with the sulfonic acid derivative (III) can be carried out according to a conventional method.

The reaction of the amine compound (II) or a salt thereof with the sulfonic acid derivative (III) can be carried out, for example, in a solvent, if necessary, in the presence of an acid receptor. As the acid receptor, there may be mentioned alkali metal carbonates such as potassium carbonate and sodium carbonate; alkali metal hydrogen carbonates such as sodium hydrogen carbonate; alkali metal hydroxides such as sodium hydroxide and potassium hydroxide; tri-lower alkylamines such as triethylamine, tributylamine and diisopropylethylamine; tertiary amines such as 1,4-diazabicyclo-[2.2.2]-octane, 1,5-diazabicyclo[4.3.0]non-5-ene, 1,8-diazabicyclo[5.4.0]undec-7-ene; and aromatic amines such as pyridine, lutidine, collidine and dimethylaniline. The solvent may be any inert solvent which does not exert bad influence on the reaction, and there may be used suitably, for example, halogen type solvents such as chloroform, dichloromethane and dichloroethane; aromatic hydrocarbons such as toluene and xylene; ether type solvents such as tetrahydrofuran, dioxane, diethyl ether and 1,2-dimethoxyethane; ketone type solvents such as acetone and methyl ethyl ketone; ester type solvents such as ethyl acetate and butyl acetate; aromatic amine type solvents such as pyridine, 2,6-lutidine and collidine; amide type solvents such as dimethylformamide, dimethylacetamide and 1,3-dimethyl-2-imidazolidinone; mixtures of these solvents; and mixtures of these solvents and water. The reaction can be carried out under cooling to under heating and proceeds preferably, for example, at −30° C. to 150° C., particularly at −10° C. to room temperature.

Method (B)

The oxidation of the compound (IV) can be carried out according to a conventional method and can be carried out preferably by, for example, treating the compound (IV) with sodium 3-nitrobenzenesulfonate in a suitable solvent under basic conditions; subjecting it to oxidation in a hydrogen bromide-acetic acid solution under acidic conditions by using dimethylsulfoxide; or halogenating it with bromide, chloride or the like and then subjecting the halogenated compound to dehydrohalogenation.

As the solvent, there may be used suitably water, acetic acid, propionic acid, trifluoroacetic acid, methanesulfonic acid and a hydrogen bromide-acetic acid solution.

In the reactions of the present invention, by using an optical isomer as the starting compound (II) or (IV), a corresponding optically active desired compound (I) can be obtained without racemization.

The starting compound (II) is a novel compound and can be prepared by, for example, if necessary after protecting an amino group of a compound represented by the formula (V):

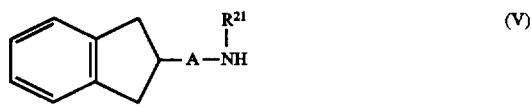

wherein $R^{21}$ represents hydrogen atom or a lower alkyl group and A has the same meaning as defined above, reacting said compound with a compound represented by the formula (VI):

wherein $R^3$ represents an ester residue; and Z represents a halogen atom, removing the ester residue and the protective group for the amino group from the resulting compound, then reacting the compound with hydrazine and when $R^{21}$ represents hydrogen atom, if necessary, further alkylating the amino group of the compound (for example, reductive alkylating it with the corresponding aldehyde compounds in the presence of an appropriate reducing agent such as sodium borohydride ($NaBH_4$), sodium triacetoxyborohydride ($NaB(OCOCH_3)_3H$)) to obtain a compound represented by the formula (VII):

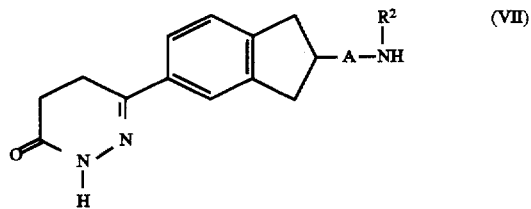

wherein $R^2$ and A have the same meanings as defined above, and oxidizing said compound in the same manner as in Method (B).

The starting compound (IV) can be prepared by reacting the compound (VII) with the compound (III) in the same manner as in Method (A).

In the present specification, the lower alkyl group means an alkyl group having 1 to 6 carbon atoms, preferably 1 to 4 carbon atoms. The lower alkylene group means an alkylene group having 1 to 10 carbon atoms, preferably 1 to 6 carbon atoms. The lower alkenyl group means an alkenyl group having 2 to 7 carbon atoms, preferably 2 to 5 carbon atoms. The lower alkyl group, lower alkylene group and lower alkenyl group include straight ones and branched ones.

EXAMPLES

The present invention is described in detail by referring to Examples.

Test example (Action on rat glomerular nephritis)

Rabbits were immunized several times with a renal glomerular basement membrane fraction obtained from WKY strain rats and an adjuvant. Thereafter, blood was collected to obtain a nephrotoxic serum (NTS). This NTS was diluted by 50 times with physiological saline, and the diluted NTS was once administered intravenously to male WKY rats of 8 weeks old in a dose of 2.5 ml per 1 kg of body weight to induce nephritis. In normal group of rats, the same volume of physiological saline was intravenously administered.

In the experiment, one group consisted of 6 rats, and each compound to be tested was suspended in water with small amount of Tween 80 (trade name, produced by Nacalai Tesque Co.), and was orally administered to the test group of rats at a dose of 30 mg/kg/10 ml twice a day for 8 days. In normal group and control group of rats, the same volume of water was orally administered instead of the test compound. After 7 days, the rats were placed in metabolic cages and urine was collected for 24 hours. Concentrations of protein in urine were measured by the sulfosalicylic acid method to determine amounts of protein excreted in the urine (mg/day). The inhibition rate of excretion of protein were calculated by the following equation.

$$\text{Inhibition rate (\%)} = 100 - \frac{\left(\begin{array}{c}\text{amount of ex-}\\\text{creted protein}\\\text{in test group}\end{array}\right) - \left(\begin{array}{c}\text{amount of ex-}\\\text{created protein}\\\text{in normal group}\end{array}\right)}{\left(\begin{array}{c}\text{amount of ex-}\\\text{creted protein}\\\text{in control group}\end{array}\right) - \left(\begin{array}{c}\text{amont of ex-}\\\text{created protein}\\\text{in normal group}\end{array}\right)} \times 100$$

The results are shown in Table 1. As seen in Table 1, inhibition rate of the protein excretion of the group which had been administered the test compound was about 60 to 90%.

TABLE 1

| Compound tested*) (Example No.) | Inhibition rate (%) |
| --- | --- |
| 4 | 61.5 |
| 6 | 65.1 |
| 7 | 77.2 |
| 8 | 71.6 |
| 12 | 67.5 |
| 19 | 91.8 |

*)The compounds obtained in Examples described below were used as compounds to be tested in the experiment.

Example 1

In a mixed solution of 30 ml of ethyl acetate and 30 ml of tetrahydrofuran was suspended 3.22 g of 2-aminomethyl-5-[pyridazin-3(2H)-on-6-yl]indane hydrobromide. A sodium carbonate aqueous solution (5.30 g/30 ml of water) was added to the suspension. Under ice cooling, 3.32 g of ethanesulfonyl chloride dissolved in 10 ml of tetrahydrofuran was added to the mixture, and the resulting mixture was stirred for 3 hours. 300 ml of ethyl acetate was added to the mixture. After the organic layer was collected by separation, washed with water and dried, and the solvent was removed. The residue was purified by silica gel column chromatography (chloroform-methanol (100:3)) to obtain 2.75 g of 2-(ethylsulfonylaminomethyl)-5-[pyridazin-3(2H)-on-6-yl]indane.

m.p.: 170° to 172° C.

Examples 2 to 12

By treating the corresponding starting compounds in the same manner as in Example 1, compounds shown in Table 2 were obtained.

TABLE 2

$$\text{[indane-pyridazinone core]} - A-N(R^2)-SO_2-R^1$$

| Example No. | $R^1$ | $R^2$ | —A— | Physical properties |
| --- | --- | --- | --- | --- |
| 2 | -n-$C_3H_7$ | H | —$CH_2$— | m.p. 166 to 168° C. |
| 3 | -n-$C_4H_9$ | H | —$CH_2$— | m.p. 182 to 184° C. |
| 4 | —CH=$CH_2$ | H | —$CH_2$— | m.p. 193 to 194° C. |
| 5 | —CH=$CH_2$ | -n-$C_3H_7$ | —$CH_2$— | m.p. 156 to 158° C. |
| 6 | —$C_2H_5$ | H | —$(CH_2)_2$— | m.p. 153 to 154° C. |
| 7 | -n-$C_3H_7$ | H | —$(CH_2)_2$— | m.p. 167 to 168° C. |
| 8 | —CH=$CH_2$ | H | —$(CH_2)_2$— | m.p. 158 to 160° C. |
| 9 | —CH=$CH_2$ | -n-$C_3H_7$ | —$(CH_2)_2$— | m.p. 122 to 124° C. |
| 10 | —$CH_3$ | H | —$(CH_2)_4$— | m.p. 157 to 159° C. |
| 11 | -n-$C_3H_7$ | H | —$(CH_2)_4$— | m.p. 100 to 101° C. (decomposed) |
| 12 | —CH=$CH_2$ | H | —$(CH_2)_4$— | m.p. 144 to 145° C. |

Example 13

25 ml of 30% hydrogen bromide-acetic acid and 1.3 ml of dimethyl sulfoxide were added to 5.24 g of 2-(propylsulfonylaminomethyl)-5-[4,5-dihydropyridazin-3(2H)-on-6-yl]indane suspended in 60 ml of acetic acid. The mixture was stirred at room temperature for 2 hours. 150 ml of isopropyl ether was added to the mixture, and crystals precipitated were collected by filtration, washed with water, dried and then recrystallized from methanol to obtain 4.82 g of 2-(propylsulfonylaminomethyl)-5-[pyridazin-3(2H)-on-6-yl]indane. This compound had the same physical properties as those of the compound obtained in Example 2.

Examples 14 to 18

By treating the corresponding starting compounds in the same manner as in Example 13, compounds shown in Table 3 were obtained.

TABLE 3

![structure with R², A-N-SO₂-R¹ substituents on indane-pyridazinone]

| Example No. | R¹ | R² | —A— | Physical properties |
|---|---|---|---|---|
| 14 | —CH=CH₂ | H | —CH₂— | the same as those of the compound obtained in Example 4 |
| 15 | —C₂H₅ | H | —(CH₂)₂— | the same as those of the compound obtained in Example 6 |
| 16 | -n-C₃H₇ | H | —(CH₂)₂— | the same as those of the compound obtained in Example 7 |
| 17 | —CH=CH₂ | H | —(CH₂)₄— | the same as those of the compound obtained in Example 12 |
| 18 | pyridyl | H | —(CH₂)₂— | m.p. 192 to 193° C. |

Examples 19 to 27

By treating the corresponding starting compounds in the same manner as in Example 1, compounds shown in Table 4 were obtained.

TABLE 4

| Example No. | R¹ | R² | —A— | Physical properties |
|---|---|---|---|---|
| 19 | —CH=CH₂ | H | —(CH₂)₃— | m.p. 147 to 149° C. |
| 20 | -n-C₃H₇ | H | —(CH₂)₃— | m.p. 158 to 161° C. |
| 21 | -n-C₃H₇ | -n-C₃H₇ | —(CH₂)₃— | m.p. 122 to 124° C. |
| 22 | pyridyl | H | —(CH₂)₂— | the same as those of the compound obtained in Example 18 |
| 23 | —CH=CH₂ | H | —(CH₂)₅— | m.p. 148 to 149° C. |
| 24 | —CH=CH₂ | H | —(CH₂)₆— | m.p. 118 to 120° C. |
| 25 | -n-C₃H₇ | -n-C₃H₇ | —(CH₂)₂— | m.p. 138 to 139° C. |
| 26 | —CH=CH₂ | -n-C₃H₇ | —(CH₂)₃— | m.p. 132 to 134° C. |
| 27 | —CH=CH₂ | -n-C₃H₇ | —(CH₂)₄— | m.p. 163 to 164° C. |

Reference example 1

(1) 46.4 g of oxalyl chloride and 2 drops of dimethylformamide were added to 48.3 g of monomethyl succinate dissolved in 840 ml of dichloroethane. The mixture was stirred at room temperature for 5 hours. Then, under ice cooling, 34.6 g of 2-(acetylaminomethyl)indane dissolved in 280 ml of dichloroethane and 97.6 g of anhydrous aluminum chloride were added to the reaction mixture. After the mixture was stirred for 1 hour, the reaction mixture was poured into ice water. After the organic layer was collected by separation, washed with water and dried, the solvent was removed to obtain 51.8 g of 2-(acetylaminomethyl)-5-(3-methoxycarbonylpropionyl)indane. m.p.: 139° to 140° C.

(2) 51.8 g of the compound obtained was suspended in 800 ml of 10N hydrochloric acid, and the mixture was refluxed under heating overnight. After the reaction mixture was concentrated and cooled, precipitated crystals (48.5 g) were collected by filtration. The crystals were suspended in 300 ml of acetic acid, and 30 g of hydrazine monohydrate was added to the suspension. The mixture was refluxed under heating for 4 hours. After cooling, diethyl ether was added to the mixture, and crystals precipitated were collected by filtration. The crystals obtained were suspended in water, adjusted to pH 9 with a 10% aqueous sodium hydroxide solution and then extracted with chloroform. After the organic layer was washed with water and dried, the solvent was removed. The residue was recrystallized from methanol to obtain 35.3 g of 2-aminomethyl-5-[4,5-dihydropyridazin-3(2H)-on-6-yl]indane.

m.p.: 170° to 171° C.

(3) 4.90 g of the compound obtained was suspended in 20 ml of acetic acid, and 50 ml of 30% hydrogen bromide-acetic acid and 2.8 g of methylsulfoxide were added to the suspension. The mixture was stirred for 3 hours. 300 ml of isopropyl ether was added to the mixture, and crystals precipitated were collected by filtration. The crude crystals obtained were recrystallized from methanol to obtain 5.11 g of 2-aminomethyl-5-[pyridazin-3(2H)-on-6-yl]indane hydrobromide.

m.p.: >300° C.

Reference example 2

(1) 2-[2-(Acetylamino)ethyl]indane was treated in the same manner as in Reference example 1-(1) to obtain 2-[2-(acetylamino) ethyl]-5-(3-methoxycarbonylpropionyl) indane.

m.p.: 96° to 97° C.

(2) The compound obtained was treated in the same manner as in Reference example 1-(2) to obtain 2-(2-aminoethyl)-5-[4,5-dihydropyridazin-3(2H)-on-6-yl] indane.

m.p.: 189° to 190° C.

(3) The compound obtained was treated in the same manner as in Reference 1-(3) to obtain 2-(2-aminoethyl)-5-[pyridazin-3(2H)-on-6-yl]indane hydrobromide.

m.p.: 279° to 280° C. (decomposed)

Reference example 3

(1) Under cooling at −78° C., 1.5M diisobutyl aluminum hydride (DIBAH) dissolved in 65 ml of toluene was added to 19.34 g of ethyl 2-indanacetate dissolved in 200 ml of toluene. The mixture was stirred at the same temperature for 1.5 hours. A 15% sodium sulfite aqueous solution was added to the mixture. After the organic layer was collected by separation, washed and dried, the solvent was removed. The residue was purified by silica gel column chromatography (hexane-ethyl acetate (10:1)) to obtain 13.58 g of 2-indanacetaldehyde.

IR (neat) cm⁻¹: 1725
FAB-MS (m/Z): 161 (MH⁺)

(2) 3.90 g of 63% sodium hydride was suspended in 60 ml of tetrahydrofuran, and 22.8 g of ethyl diethylphosphonoacetate dissolved in 100 ml of tetrahydrofuran was added dropwise to the suspension under water cooling. The mixture was stirred at the same temperature for 30 minutes. 13.58 g of 2-indanacetaldehyde dissolved in 100 ml of tetrahydrofuran was added dropwise to said mixture. The resulting mixture was stirred at the same temperature for 1 hour and further stirred at room temperature for 1 hour. The reaction mixture was poured into ice water and extracted with ethyl acetate. After the ethyl acetate layer was washed and dried, the solvent was removed. The residue was purified by silica gel column chromatography (hexane-ethyl acetate (20:1)) to obtain 19.22 g of ethyl 2-indanecrotonate.

IR (neat) $cm^{-1}$: 1700, 1655

FAB-MS (m/Z): 231 (MH$^+$)

(3) 2.0 g of 10% palladium-carbon was added to 19.22 g of the compound obtained dissolved in 200 ml of ethanol to effect catalytic hydrogenation at room temperature and normal pressure. After 1.5 hours, the catalyst was removed and ethanol was removed to obtain 19.24 g of ethyl 2-indanebutyrate.

IR (neat) $cm^{-1}$: 1740

MS (m/Z): 232 (M$^+$)

(4) A sodium hydroxide aqueous solution (5.15 g/30 ml of water) was added to 19.21 g of the compound obtained dissolved in 50 ml of ethanol. The mixture was stirred at room temperature for 1 hour. After ethanol was removed, the aqueous layer was made weakly acidic with 10% hydrochloric acid and extracted with ethyl acetate. After the ethyl acetate layer was washed and dried, the solvent was removed to obtain 16.87 g of 2-indanebutyric acid.

m.p.: 74° to 75° C.

(5) Three drops of dimethylformamide was added to 16.84 g of the compound obtained and 11.67 g of oxalyl chloride dissolved in 200 ml of tetrahydrofuran. The mixture was stirred for 1.5 hours. The solvent and excessive oxalyl chloride were removed. The residue was dissolved in 10 ml of tetrahydrofuran, and the solution was cooled with ice and added dropwise to 100 ml of a 28% ammonia aqueous solution. The mixture was stirred at the same temperature for 2 hours. Crystals formed were collected by filtration, washed with water and then dried to obtain 14.46 g of 2-indanebutyric amide.

m.p.: 116° to 118° C.

(6) Under ice cooling, 14.42 g of 2-indanebutyric amide was added to 3.23 g of lithium aluminum hydroxide suspended in 200 ml of tetrahydrofuran. The mixture was refluxed under heating for 1.5 hours. After cooling, a 50% Rochelle salt aqueous solution was added to the mixture, and insolubles precipitated were removed by filtration. The filtrate was concentrated and solidified. The residue was dissolved in 50 ml of tetrahydrofuran, and hydrogen chloride-dioxane was added to the solution. Crystals precipitated were collected by filtration to obtain 12.82 g of 2-(4-aminobutyl)indane hydrochloride.

m.p.: 184° to 186° C.

(7) Under ice cooling, 5.42 g of acetyl chloride dissolved in 20 ml of dichloromethane was added dropwise to 12.74 g of the compound obtained and 13.91 g of triethylamine suspended in 100 ml of dichloromethane. The mixture was stirred at the same temperature for 1 hour. After the reaction mixture was washed and dried, the solvent was removed. The resulting crude crystals were recrystallized from ethyl acetate-isopropyl ether to obtain 12.0 g of 2-(4-acetylaminobutyl) indane.

m.p.: 83° to 84° C.

(8) The compound obtained was treated in the same manner as in Reference example 1-(1) to obtain 2-(4-acetylamino-butyl)- 5-(3-methoxycarbonylpropionyl) indane.

m.p.: 94° to 95° C.

(9) The compound obtained was treated in the same manner as in Reference example 1-(2) to obtain 2-(4-aminobutyl)-5-[4,5-dihydropyridazin-3(2H)-on-6-yl] indane.

m.p.: 153° to 155° C.

(10) The compound obtained was treated in the same manner as in Reference example 1-(3) to obtain 2-(4-aminobutyl)-5-[pyridazin-3(2H)-on-6-yl]indane.

m.p.: 279° to 281° C.

Reference example 4

(1) 1.51 g of propanal dissolved in 5 ml of methanol was added dropwise to 6.15 g of 2-aminomethyl-5-[4,5-dihydropyridazin-3(2H)-on-6-yl]indane dissolved in 60 ml of methanol. The mixture was stirred at room temperature for 30 minutes. Then, under ice cooling, 1.03 g of sodium borohydride was added to the mixture. The resulting mixture was stirred at the same temperature for 20 minutes and then stirred at room temperature for 1 hour. After methanol was removed, water was added to the residue, and the residue was extracted with ethyl acetate. After the organic layer was washed with water and dried, the solvent was removed. The residue was purified by silica gel column chromatography (solvent: chloroform-methanol (15:1)) to obtain 5.22 g of 2-(propylaminomethyl)-5-[4,5-dihydropyridazin-3(2H)-on-6-yl]indane.

m.p.: 82° to 84° C.

(2) 5.08 g of the compound obtained was treated in the same manner as in Reference example 1-(3) to obtain 4.52 g of 2-(propylamino)methyl-5-[pyridazin-3(2H)-on-6-yl] indane hydrobromide. Then, the compound obtained was treated with a 10% sodium hydroxide aqueous solution to obtain 3.13 g of 2-(propylaminomethyl)-5-[pyridazin-3(2H) -on-6-yl]indane.

m.p.: 144° to 146° C.

Reference example 5

(1) 2-(2-Aminoethyl)-5-[4,5-dihydropyridazin-3(2H)-on-6-yl]indane was treated in the same manner as in Reference example 4-(1) to obtain 2-[2-(propylamino)ethyl]-5-[4,5-dihydropyridazin-3(2H)-on-6-yl]indane.

m.p.: 123° to 124° C.

(2) The compound obtained was treated in the same manner as in Reference example 1-(3) to obtain 2-[2-(propylamino)-ethyl]-5-[pyridazin-3(2H)-on-6-yl]indane hydrobromide. Then, the compound obtained was treated with a 10% sodium hydroxide aqueous solution to obtain 2-[2-(propylamino)-ethyl]-5-[pyridazin-3(2H)-on-6-yl] indane.

m.p.: 150° to 151° C.

Reference example 6

5.53 g of triethylamine was added to 6.03 g of 2-aminomethyl-5-[4,5-dihydropyridazin-3(2H)-on-6-yl] indane suspended in 60 ml of 1,3-dimethyl-2-imidazolidinone, and then 5.10 g of propanesulfonyl chloride dissolved in 20 ml of tetrahydrofuran was added to the mixture. The resulting mixture was stirred at room temperature for 30 minutes. The reaction mixture was poured into ice water, and crystals precipitated were collected by filtration. The precipitated crystals were recrystallized from methanol-acetonitrile to obtain 5.34 g of 2-(propylsulfonylaminomethyl)-5-[4,5-dihydropyridazin-3 (2H)-on-6-yl]indane.

m.p.: 158° to 159° C.

Reference examples 7 to 13

By treating the corresponding starting compounds in the same manner as in Reference example 6, compounds shown in Table 5 were obtained.

TABLE 5

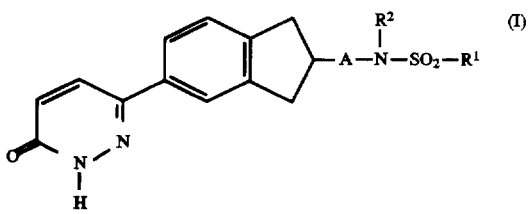

| Reference example No. | $R^1$ | $R^2$ | —A— | Physical properties |
|---|---|---|---|---|
| 7 | —CH=CH$_2$ | H | —CH$_2$— | m.p. 163 to 165° C. |
| 8 | -n-C$_3$H$_7$ | H | —(CH$_2$)$_2$— | m.p. 168 to 169° C. |
| 9 | —C$_2$H$_5$ | H | —(CH$_2$)$_2$— | m.p. 170 to 171° C. |
| 10 | —CH=CH$_2$ | H | —(CH$_2$)$_2$— | m.p. 171 to 173° C. |
| 11 | -n-C$_3$H$_7$ | H | —(CH$_2$)$_4$— | m.p. 97 to 99° C. |
| 12 | —CH=CH$_2$ | H | —(CH$_2$)$_4$— | m.p. 145 to 147° C. |
| 13 | (pyridyl) | H | —(CH$_2$)$_2$— | m.p. 189 to 190° C. |

The desired indane derivative (I) or the present invention and a pharmaceutically acceptable salt thereof have excellent actions of protecting from endotoxin shock and/or excellent actions of curing nephritis so that they are useful as, for example, an agent for curing endotoxin shock which occurs in a patient seriously infected with gram-negative bacteria or an agent for curing nephritis.

Further, the desired compound (I) of the present invention has low toxicity so that it can be a medicine having high safety.

We claim:

1. An indane compound represented by the formula:

(I)

wherein $R^1$ represents a $C_{1-6}$ alkyl group or a $C_{2-7}$ alkenyl group; $R^2$ represents a hydrogen atom or a $C_{1-6}$ alkyl group; and A represents a $C_{1-10}$ alkylene group, or a pharmaceutically acceptable salt thereof.

2. The indane compound according to claim 1, wherein $R^1$ represents a $C_{1-4}$ alkyl group or a $C_{2-5}$ alkenyl group.

3. The indane compound according to claim 1, wherein $R^2$ represents a hydrogen atom.

4. The indane compound according to claim 1, wherein $R^2$ represents a $C_{1-6}$ alkyl group.

5. The indane compound according to claim 1, wherein $R^1$ represents an alkyl group having 1 to 4 carbon atoms or an alkenyl group having 2 to 5 carbon atoms; $R^2$ represents a hydrogen atom or an alkyl group having 1 to 4 carbon atoms; and A represents an alkylene group having 1 to 10 carbon atoms.

6. The indane compound according to claim 1, wherein $R^1$ represents an alkyl group having 1 to 4 carbon atoms or an alkenyl group having 2 to 5 carbon atoms; $R^2$ represents a hydrogen atom or an alkyl group having 1 to 4 carbon atoms; and A represents an alkylene group having 1 to 6 carbon atoms.

7. The indane compound according to claim 1, wherein $R^1$ represents —CH$_3$, —C$_2$H$_5$, —n—C$_3$H$_7$, —CH(CH$_3$)$_2$, —n—C$_4$H$_9$ or —CH=CH$_2$; $R^2$ represents a hydrogen atom, —CH$_3$, —C$_2$H$_5$ or —n—C$_3$H$_7$; and A represents —CH$_2$—, —(CH$_2$)$_2$—, —(CH$_2$)$_3$—, —(CH$_2$)$_4$—, —(CH$_2$)$_5$— or —(CH$_2$)$_6$—.

8. The indane compound according to claim 1, wherein the compound is selected from the group consisting of 2(ethylsulfonylaminomethyl)-5-[pyridazin-3(2H)-on-6-yl] indane, 2-(propylsulfonylaminomethyl)-5-5[pyridazin-3 (2H)-on-6-yl]indane, 2-(vinylsulfonylaminomethyl)-5-[pyridazin-3(2H)-on-6-yl]indane, N-n-propyl-2-(vinylsulfonylaminomethyl)-5-[pyridazin-3(2H)-on-6-yl] indane, 2-(ethylsulfonylaminoethyl)-5-[pyridazin-3(2H)-on-6-yl]indane, 2(propylsulfonylaminoethyl)-5-[pyridazin-3(2H)-on-6-yl]indane, 2-(vinylsulfonylaminoethyl)-5-[pyridazin-3(2H)-on-6-yl]indane, 2-(vinylsulfonylaminobutyl)-5-[pyridazin3(2H)-on-6-yl] indane, 2-(vinylsulfonylaminopropyl)-5-[pyridazin-3(2H)-on-6-yl]indane, N-n-propyl-2-(propylsulfonylaminoethyl)-5-[pyridazin-3(2H)-on-6-yl]indane and N-n-propyl-2-(vinylsulfonylaminopropyl)-5-[pyridazin-3(2H)-on-6-yl] indane.

9. 2-(Vinylsulfonylaminobutyl)-5-[pyridazin-3(2H)-on-6-yl]indane or a pharmaceutically acceptable salt thereof.

10. 2-(Propylsulfonylaminoethyl)-5-[pyridazin-3(2H)-on-6-yl]indane or a pharmaceutically acceptable salt thereof.

11. A pharmaceutical composition which comprises an endotoxin shock and/or nephritis-treatment amount of the compound as set forth in claim 1 in admixture with a conventional pharmaceutically acceptable carrier or diluent.

12. A method for the prophylaxis or treatment of endotoxin shock and/or nephritis in a patient, which comprises administering to said patient an endotoxin shock and/or nephritis-treatment amount of the compound as set forth in claim 1.

13. A pharmaceutical composition which comprises a nephritis-treatment amount of the compound as set forth in claim 1 in admixture with a conventional pharmaceutically acceptable carrier or diluent.

14. A pharmaceutical composition which comprises a glomerular nephritis-treatment amount of the compound as set forth in claim 1 in admixture with a conventional pharmaceutically acceptable carrier or diluent.

15. A method for the prophylaxis or treatment of nephritis in a patient, which comprises administering to said patient an effective nephritis-treatment amount of the compound as set forth in claim 1.

16. A method for the prophylaxis or treatment of glomerular nephritis in a patient, which comprises administering to said patient a glomerular nephritis-treatment amount of the compound as set forth in claim 1.

17. A method for the prophylaxis or treatment of endotoxin shock and/or nephritis in a patient, which comprises administering to said patient an endotoxin shock and/or nephritis-treatment amount of the compound as set forth in claim 1.

18. A method for the treatment of nephritis in a patient, which comprises administering to said patient a nephritis-treatment amount of the compound as set forth in claim 1.

19. A method for the treatment of glomerular nephritis in a patient, which comprises administering to said patient a glomerular nephritis-treatment amount of the compound as set forth in claim 1.

20. A method for the prophylaxis or treatment of proteinuria in a patient, which comprises administering to said patient a proteinuria-treatment amount of the compound as set forth in claim 1.

21. A method for the treatment of proteinuria in a patient which comprises administering to said patient a proteinuria-treatment amount of the compound as set forth in claim 1.

* * * * *

UNITED STATES PATENT AND TRADEMARK OFFICE
CERTIFICATE OF CORRECTION

PATENT NO. : 5,686,452
DATED : November 11, 1997
INVENTOR(S) : Akihiko ISHIDA et al.

It is certified that error appears in the above-identified patent and that said Letters Patent is hereby corrected as shown below:

on the Title page, item [30]

Change "Dec. 28, 1994" to --Dec. 28, 1993--

Signed and Sealed this

Fourteenth Day of April, 1998

Attest:

BRUCE LEHMAN

*Attesting Officer*  *Commissioner of Patents and Trademarks*